US006281264B1

(12) United States Patent
Salovey et al.

(10) Patent No.: US 6,281,264 B1
(45) Date of Patent: Aug. 28, 2001

(54) CHEMICALLY CROSSLINKED ULTRAHIGH MOLECULAR WEIGHT POLYETHYLENE FOR ARTIFICIAL HUMAN JOINTS

(75) Inventors: Ronald Salovey, Rancho Palos Verdes; Harry A. McKellop; Fu-Wen Shen, both of Los Angeles, all of CA (US)

(73) Assignees: The Orthopaedic Hospital; University of Southern California, both of Los Angeles, CA (US)

(*) Notice: Subject to any disclaimer, the term of this patent is extended or adjusted under 35 U.S.C. 154(b) by 0 days.

(21) Appl. No.: 09/406,305

(22) Filed: Sep. 27, 1999

Related U.S. Application Data

(60) Continuation of application No. 08/698,638, filed on Aug. 15, 1996, now abandoned, which is a division of application No. 08/376,953, filed on Jan. 20, 1995, now abandoned.

(51) Int. Cl.⁷ .................................................. A61F 2/00
(52) U.S. Cl. .................... 523/115; 525/333.7; 623/18.11; 623/20.14; 623/22.11; 623/22.21; 623/23.58
(58) Field of Search ............................................... 523/115

(56) References Cited

U.S. PATENT DOCUMENTS

| | | |
|---|---|---|
| 2,948,666 | 8/1960 | Lawton . |
| 3,297,641 | 1/1967 | Werber et al. . |
| 3,352,818 | 11/1967 | Meyer et al. . |
| 3,646,155 | 2/1972 | Scott ................................. 260/827 |
| 3,671,477 | 6/1972 | Nesbitt ............................... 524/424 |
| 3,758,273 | 9/1973 | Johnston et al. . |
| 3,944,536 | 3/1976 | Lupton et al. . |
| 4,055,862 | 11/1977 | Farling . |
| 4,138,382 | 2/1979 | Polmanteer . |
| 4,281,420 | 8/1981 | Raab . |
| 4,390,666 | 6/1983 | Moriguchi ........................... 525/194 |
| 4,483,333 | 11/1984 | Wartman ............................. 128/90 |
| 4,518,552 | 5/1985 | Matsuo et al. ........................ 264/126 |
| 4,539,374 | 9/1985 | Fenton et al. ......................... 525/240 |
| 4,582,656 | 4/1986 | Hoffman . |
| 4,655,769 | 4/1987 | Zachariades . |
| 4,668,527 | 5/1987 | Fujita et al. . |
| 4,743,493 | 5/1988 | Sioshansi et al. . |
| 4,747,990 | 5/1988 | Gaussens et al. . |
| 4,816,517 | 3/1989 | Wilkus ............................... 524/520 |
| 4,876,049 | 10/1989 | Aoyama et al. . |
| 4,888,369 | 12/1989 | Moore, Jr. ........................... 524/100 |
| 4,902,460 | 2/1990 | Yagi ................................. 264/83 |
| 4,944,974 | 7/1990 | Zachariades . |
| 5,024,670 | 6/1991 | Smith et al. . |
| 5,037,928 | 8/1991 | Li et al. . |
| 5,130,376 | 7/1992 | Shih ................................. 525/240 |
| 5,133,757 | 7/1992 | Sioshansi et al. ..................... 623/18 |
| 5,160,464 | 11/1992 | Ward et al. . |
| 5,160,472 | 11/1992 | Zachariades . |
| 5,180,394 | 1/1993 | Davidson et al. . |
| 5,192,323 | 3/1993 | Shetty et al. . |
| 5,200,439 | 4/1993 | Asanuma . |
| 5,210,130 | 5/1993 | Howard . |
| 5,236,563 | 8/1993 | Loh ................................. 204/165 |
| 5,356,998 | 10/1994 | Hobes . |
| 5,407,623 | 4/1995 | Zachariades et al. . |
| 5,414,049 | 5/1995 | Sun et al. ........................... 525/333.7 |
| 5,439,949 | 8/1995 | Lucas et al. . |
| 5,449,745 | 9/1995 | Sun et al. ........................... 528/483 |
| 5,466,530 | 11/1995 | England et al. . |
| 5,478,906 | 12/1995 | Howard, Jr. . |
| 5,480,683 | 1/1996 | Chabrol et al. . |
| 5,508,319 | 4/1996 | DeNicola ............................ 526/352 |
| 5,515,590 | 5/1996 | Pienkowski . |
| 5,549,698 | 8/1996 | Averill et al. . |
| 5,549,700 | 8/1996 | Graham et al. . |
| 5,609,638 | 3/1997 | Price et al. . |
| 5,645,882 | 7/1997 | Llanos . |
| 5,702,448 | 12/1997 | Buechel et al. . |
| 5,702,456 | 12/1997 | Pienkowski . |
| 5,879,400 | * 3/1999 | Merrill .............................. 623/22 |

FOREIGN PATENT DOCUMENTS

| | | |
|---|---|---|
| A-1001574 | 12/1989 | (BE) . |
| 0 169 259 | 7/1984 | (EP) . |
| 0 373 800 A1 | 6/1990 | (EP) . |
| 58-157830A | 9/1983 | (JP) . |
| A-59 168 050 | 9/1984 | (JP) . |
| A-62 243 634 | 1/1987 | (JP) . |
| 04-198242 | 7/1992 | (JP) . |
| A-04 185651 | 7/1992 | (JP) . |
| WO 95/21212 | 8/1995 | (WO) . |
| WO 96/09330 | 3/1996 | (WO) . |

OTHER PUBLICATIONS

Appleby, R.W., et al., "Post–gamma irradiation cross–linking of polyethylene tape by acetylene treatment", J. Material Sci. 29: 227–231 (1994).

Streicher, "Influence of Ionizing Irradiation in Air and Nitrogen for Sterilization of Surgical Grade Polyethylene for Implants", Radiat. Phys. Chem., vol. 31, Nos. 4–6, pp. 693–698 (1988).

Roe et al., "Effect of Radiation Sterilization and Aging on Ultrahigh Molecular Weight Polyethylene", J. Biomed. Materials Res., 15: 209–230 (1981).

Pleiss et al., "The Improvement of Polyethylene Prostheses Through Radiation Crosslinking", Radiat. Phys. Chem., 9: 647–652 (1977).

Streicher, "The Behavior of UHMW–PE when Subjected to Sterilization by Ionizing Radiation", Ultra–High Molecular Weight Polyethylene as Biomaterial in Orthopedic Surgery, pp. 66–73 (1990).

(List continued on next page.)

Primary Examiner—Paul R. Michl
(74) Attorney, Agent, or Firm—Wean Khing Wong

(57) ABSTRACT

The present invention discloses a method for enhancing the wear-resistance of polymers by crosslinking them, especially before irradiation sterilization. In particular, this invention presents the use of chemically crosslinked ultrahigh molecular weight polyethylene in in vivo implants.

72 Claims, 4 Drawing Sheets

OTHER PUBLICATIONS

Saunders, C. et al., "Raidation Effects on Microorgansims and Polymers for Medical Products," Medical Device & Diagnostic Industry, pp. 89–92, 222 (1993).

Kang et al., "The Radiation Chemistry of Polyethylene. IX. Temperature Coefficient of Cross–Linking and Other Effects", J. Amer Chem Society 89 (9): 1980–1986 (1967).

Rose et al., "Radiation Sterilization and the Wear Rate of Polyethylene", J. Orthopaedic Res. Society, 2(4): 393–400 (1984).

Oonishi, H. et al., Super Low Wear Cross–Linked UHM-WPE by Heavy High–Dose Gamma Radiation, WPOA 2nd Congress of Hip Section, p. 61, 1996.

Jahan et al., "Combined chemical and mechanical effects on free radicals in UHMWPE joints during implantation", J. Biomed Material Res., 25: 1005–1016 (1991).

Standard Practice for Dosimetry in an Electron Beam Facility for Radiation Processing at Energies Between 300 keV and 25 keV, Am Soc for Testing & Materials, Designation: E1649–94, 870–888 (1995).

Oonishi, H. et al., "Improvement Of Polyethylene by Irradiation in Artificial Joints", Radia Phys Chem, 39(6): 495–504 (1992).

Oonishi, H. et al., "The Low Wear of Cross–Linked Polyethylene Socket in Total Hip Prosthees", Encyclopedic Handbook of Biomaterials & Bioengineering, vol. 2, Marcel Dekker, Inc., 1853–1868 (1995).

Atkinson, J., et al., "The nature of silane cross–linked HDPE is discussed. Creep and wear tests indicate its potential as a possible replacement for high molecular weight polyethylene in prostheses", Polymers in Medicine and Surgery, Conf. held by Plastics and Rubber Institute and Biologidal Engineering Soc., UK, Sep., 1986, P4/1–P4/9.

Jones, W., et al., "Effect of γ Irradiation on the Friction and Wear of Ultrahigh Molecular Weight Polyethylene", Wear 70: 77–92 (1981).

Gent, A., et al., "Elastic Behavior, Birefringence, and Swelling of Amorphous Polyethylene Networks", J. Polymer Sci 5: 47–60 (1967).

Zoepfl, F., et al., "Differential Scanning Calorimetry Studies of Irradiated Polyethylene: I. Melting Temperatures and Fusion Endotherms", J. Polymer Sci Polym. Chem. Ed. 22: 2017–2032 (1984).

Zoepfl, F., et al., Differential Scanning Calorimetry Studies of Irradiated Polyethylene: II. The Effect of Oxygen, J. Polymer Sci Polym. Chem. Ed. 22: 2032–2045 (1984).

Mandelkern, L., et al., Fusion of Polymer Networks Formed from Linear Polyethylene: Effect of Intermolecular Order: contribution from the General Electric Research Laboratory and from the Polymer Structure Section, National Bureau of Standards 82: 46–53 (1960).

Matsubara, K., et al., "The Wear Properties of High–Density Polyethylene Irradiated by Gamma Rays", Wear, 10: 214 (1967).

McKellop, H., et al., "Increased Wear of UHMW Polyethylene After Gamma Radiation Sterilization", Trans. 26th Ann. ORS, Atlanta, Georgia, Feb. 5–7 (1980).

McKellop, H., "The Effect of Radiation and Ethylene Oxide Sterilization on the Wear of UHMW Polyethylene," 7th European Conference on Biomaterials, Sep. 8–11, 1987.

"Poly Two Carbon–Polyethylene Composite–A Carbon Fiber Reinforced Molded Ultra–High Molecular Weight Polyethylene", Technical Report, Zimmer (a Bristol–Myers Squibb Company), Warsaw (1977).

Atkinson, J.R., et al., "Materials for internal prostheses: the present position and possible future developments", Biomaterials 1: 89–96 (1980).

Atkinson, J. R. et al., "Silane cross–linked polyethyelene for prosthetic applications. Part I. Certain physical and mechanical properties related to the nature of the material", Biomaterials, 4:326 (1983).

Atkinson, J. R. et al., "Silane cross–linked polyethyelene for prosthetic applications. Part II. Creep and wear behaviour and a preliminary moulding test", Biomaterials, 5:267 (1984).

Bartel, D. L., et al., "The Effect of Comformity, Thickness, and Material on Stresses in Ultra–High Molecular Weight Components for Total Hip Replacement", J. Bone & Joint Surgery, 68–A(7): 1041 (1986).

Bhateja, S.K., "Radiation–Induced Crystallinity Changes in Pressure–Crystalized Ultrahigh Molecular Weight Polyethylene", J. Macromol. Sci. Phys., B22(1): 159 (1983).

Bhateja, S.K., et a.l., "Radiation–Induced Crystallinity Changes in Linear Polyethylene", J. Polym. Sci. Polym. Phys. Ed, 21: 523 (1983).

Bhateja, S.K., et al., "Radiation–Induced Crystallinity Changes in Polyethylene Blends", J. Mater. Sci., 20: 2839 (1985).

Birkinshaw, C., et al., "The Melting Behaviour of Irradiated Polymers", Thermochimica Acta, 117: 365 (1987).

Bloebaum, R.D., et al., "Investigation of Early Surface Delamination Observed in Retrieved Heat–Pressed Tibial Inserts", Clin. Orthop., 269: 120 (1991).

Bremmer, T., et al., "Peroxide Modification of Linear Low–Density Polyethylene: A Comparison of Dialkyl Peroxides", J. Appl. Polym. Sci., 49: 785 (1993).

Brown, K.J., et al., "The Wear of Ultra–High Molecular Weight Polyethylene with Reference to Its Use in Prostheses", Plastics in Medicine & Surgery Plastics & Rubber Institute, London, 2.1 (1975).

Chen, C.J., et al., "Radiation–induced crosslinking: II. Effect on the crystalline and amorphous densities of polyethylene", Coll. & Polym. Sci., 269: 469 (1991).

Chen, Y.L., et al., "Photocrosslinking of Polyethylene. I. Photoinitiators, Crosslinking Agent, and Reaction Kinetics", J. Polym. Sci., Part A: Polym. Chem., 27: 4051 (1989).

Chen, Y. L., et al., "Photocrosslinking of Polyethylene. II. Properties of Photocrosslinked Polyethylene", J. Polym. Sci., Part A: Polym. Chem., 27: 4077 (1989).

Connelly, G. M., et al., "Fatigue Crack Propagation Behavior of Ultrahigh Molecular Weight Polyethylene", J. Orthop. Res., 2: 119 (1984).

de Boer, A. P., et al., "Polyethylene Networks Crosslinked in Solution: Preparation, Elastic Behavior, and Oriented Crystallization. I. Crosslinking in Solution", J. Polym. Sci., Polym. Phys. Ed., 14: 187 (1976).

de Boer, J., et al., "Crosslinking of Ultra–High Molecular Weight Polyethylene in the Melt by Means of 2,5–dimethyl–2,5–bis(tert–butyldioxy)–3–hexyne", Makromol. Chem., Rapid Commun., 2: 749 (1981).

de Boer, J., et al., "Crosslinking of Ultra–High Molecular Weight Polyethylene in the Melt by Means of 2,5–dimethyl–2,5–bis(tert–butyldioxy)–3–hexyne: 2. Crystallization Behaviour and Mechanical Properties", Polymer, 23: 1944 (1982).

de Boer, J., et al., "Crosslinking of Ultra–High Molecular Weight Polyethylene in the Oriented State with Dicumylperoxide", Polymer, 25: 513 (1984).

Dijkstra, D.J., et al., "Cross–linking of ultra–high molecular weight polyethylene in the melt by means of electron beam irradiation", *Polymer*, 30: 866 (1989).

Ding, Z. Y., et al., "Model Filled Polymers. VI. Determination of the Crosslink Density of Polymeric Beads by Swelling", *J. Polym. Sci., Polym. Phys.*, 29: 1035 (1991).

Eyerer, P. et al., "Property changes of UHMW polyethylene hip cup endoprostheses during implantation", *J. Biomed. Materials Res.*, 18: 1137 (1984).

Eyerer, P., "Polyethylene", *Concise Encyclopedia of Medical & Dental Implant Materials*, Pergamon Press, Oxford, 271 (1990).

Ferris, B. D., "A quantitative study of the tissue reaction and its relationship to debris production from a joint implant", *J. Exp. Path.*, 71: 367 (1990).

Gielenz, G. et al., "Crystalline and supermolecular structures in linear polyethylene irradiated with fast electrons", *Colloid & Polymer Sci.*, 260: 742 (1982).

Grobbelaar, C.J. et al., "The Radiation Improvement of Polyethylene Prosthesis", *J. Bone & Joint Surgery*, 60–B(3): 370–374 (1978).

Groodman, S., et al., "Polyethylene wear in knee arthroplasty", *Acta Orthop. Scand.*, 63(3): 358 (1992).

Grood, E.S., et al., "Analysis of retrieved implants: Crystallinity changes in ultrahigh molecular weight polyethylene", *J. Biomedical Materials Res.*, 16: 399 (1982).

Huang, D.D., et al., "Cyclic Fatigue Behaviors of UHMWPE and Enhanced UHMWPE", *Trans. 38Th Ann. Mtg., Orthop. Res. Soc.*, 17:403 (1992).

Kamel, I., et al., "A Model for Radiation–Induced Changes in Ultrahigh–Molecular–Weight–Polyethylene", *J. Polym. Sci. Polym. Phys. Ed.*, 23:2407 (1985).

Kampouris, E.M., et al., "Benzyl Peroxide as a Crosslinking Agent for Polyethylene", *J. Appl. Polym. Sci.*, 34:1216 (1987).

Kao, Y.H., "Crystallinity in chemically crosslinked low density polyethylenes: 1. Structural and fusion studies", *Polymer*, 27: 1669 (1986).

Katq, K., et al., "Structural Changes and Melting Behavior of γ–Irradiated Polyethylene", *Japanese J. Appl. Phys.*, 20: 691 (1981).

Kunert, K.A., et al., "Structural investigation of chemically crosslinked low density polyethylene", *Polymer*, 22: 1355 (1981).

Kurth, M., et al., "Effects of Radiation Sterilization on UHMW–Polyethylene", *Trans. Third World Biomaterials Congress*, 589 (1988).

Landy, M.M. et al., "Wear of Ultra–high–molecular–weight Polyethylene Components of 90 Retrieved Knee Prostheses", *J. Arthroplasty*, Supplement, 3: S73 (1988).

Lem, K., et al., "Rheological Properties of Polyethylenes Modified with Dicumyl Peroxide", *J. Appl. Polym. Sci.*, 27: 1367 (1982).

Li, S., et al., "Characterization and Description of an Enhanced Ultra High Molecular Weight Polyethylene for Orthopaedic Bearing Surfaces", *Trans. 16th Ann. Soc. Biomaterials Meeting, Charleston, SC*, 190 (1990).

Manley, T.R., et al., "The effects of varying peroxide concentration in crosslinked linear polyethylene", *Polymer*, 12:176 (1971).

McKellop, H., et al., "Friction, Lubrication and Wear of Polyethylene/Metal and Polyethylene/Ceramic Hip Prostheses on a Joint Simulator", *Fourth World Biomaterials Congress, Berlin*, Apri., 118 (1992).

Minkova, L., "DSC of γ–irradiated ultra–high molecular weight polyethylene and high density polyethylene of normal molecular weight", *Colloid & Polymer Sci.*, 266: 6 (1988).

Minkova, L., et al., "Blends of normal high density and ultra–high molecular weight polyethylene, γ–irradiated at a low dose", *Colloid & Polymer Sci.*, 268: 1018 (1990).

Nagy, E.V., et al., "A Fourier transform infrared technique for the evaluation of polyethylene orthopaedic bearing materials", *Trans. 16Th Ann. Soc. For Biomaterials Meeting, Charleston, SC* 109 (1990).

Narkis, M., et al., "Structure and Tensile Behavior of Irradiation–and Peroxide–Crosslinked Polyethylene", *J. Macromol. Sci.–Phys.*, B26 (1): 37 (1987).

Nusbaum, H. J. Et al., "The Effects of Radiation Sterilization on the Properties of Ultrahigh Molecular Weight Polyethylene", *J. Biomed. Materials Res.*, 13:557 (1979).

Oonishi, H., et al., "Improvement of Polyethylene by Irradiation in Artificial Joints", *Radiat. Phys. Chem.*, 39: 495 (1992).

Oonishi, H. et al., "In Vivo and In Vitro Wear Behaviour on Weightbearing Surfaces of Polyethylene Sockets Improved by Irradiation in Total Hip Prostheses", pp. 101–115, in *Surface Modification Technologies V*, Sudarshan T.S. et al., ed. (The Institute of Materials, 1992).

Painter, P.C., et al., "The Theory of Vibrational Spectroscopy and Its Application to Polymeric Materials", John Wiley & Sons, New York, U.S.A. (1982).

Paul, J. P., "Forces Transmitted by Joints in the Human Body", *Proc. Instn. Mech. Engrs.*, 181, Part 3J, Paper 8 (1966).

Qu, B. J., et al., "Photocross–linking of Low–Density Polyethylene. I. Kinetics and Reaction Parameters", *J. Appl. Polym. Sci.*, 48: 701 (1993).

Qu, B. J., et al., "Photocross–linking of Low–Density Polyethylene. II. Structure and Morphology", *J. Appl. Polym. Sci.*, 48:711 (1993).

Rimnac, C.M., et al., "Chemical and Mechanical Degradation of UHMWPE: Report of the Development of an in vitro Test", *J. Appl. Biomaterials*, 5:17 (1994).

Rimnac, C.M., et al., "Observations of Surface Damage and Degradation on Retrieved PCA Knee Implants", *Trans. 38Th Ann. Orthopaedic Res. Society, Washington D.C.*, 330 (1992).

Rimnac, C.M., et al., "Post–Irradiation Aging of Ultra–High Molecular Weight Polyethylene", *J. Bone & Joint Surgery*, 76–A(7):1052 (1994).

Roe, R., et al., "Effect of radiation sterilization and aging on ultrahigh molecular weight polyethylene", *J. Biomed. Mat. Res.*, 15:209 (1981).

Rose, R.M., et al., "On the True Wear Rate of Ultra–High–Molecular–Weight Polyethylene in the Total Hip Prosthesis", *J. Bone & Joint Surgery*, 62A(4): 537 (1980).

Rose, R.M., et al., "Exploratory Investigations in the Structure Dependence of the Wear Resistance of Polyethylene", *Wear*, 77:89 (1982).

Rostoker, W., et al., "The Appearances of Wear on Polyethylene—A Comparison of in vivo and in vitro Wear Surfaces", *J. Biomed. Materials Res.*, 12:317 (1978).

Seedhom, B.B., et al., "Wear of Solid Phase Formed High Density Polyethylene in Relation to the Life of Artificial Hips and Knees", *Wear*, 24:35 (1973).

Shen, C., et al., "The Friction and Wear Behavior of Irradiated Very High Molecular Weight Polyethylene", *Wear,* 30:349 (1974).

Shinde, A., et al., "Irradiation of Ultrahigh–Molecular–Weight Polyethylene", *J. Polym. Sci., Polym. Phys. Ed.,* 23:1681 (1985).

Spruiell, J. E., et al., "Methods of Experimental Physics", L. Marton & C. Marton, Eds., vol. 16, Part B, Academic Press, New York (1980).

Streicher, R.M., "Ionizing irradiation for sterilization and modification of high molecular weight polyethylenes", *Plastics & Rubber Processing & Applications,* 10:221 (1988).

Streicher, R. M., "Investigation on Sterilization and Modification of High Molecular Weight Polyethylenes by Ionizing Irradiation", *Beta–gamma* 1/89: 34–43.

Swanson, S.A.V., et al., Chapter 3, "Friction, Lubrication and Wear", *The Scientific Basis of Joint Replacement,* Pittman Medical Publishing Co., Ltd. (1977).

Wang, X., et al., "Melting of Ultrahigh Molecular Weight Polyethylene", *J. App. Polymer Sci.,* 34:593 (1987).

Wright, T.M., et al., "The effect of carbon fiber reinforcement on contact area, contact pressure, and time–dependent deformation in polyethylene tibial components", *J. Biomed. Materials Res.,* 15:719 (1981).

Zachariades, A.E., "A New Class of UHMWPE Orthopaedic Prosthetic Devices with Enhanced Mechanical Properties", Trans. Fourth World Biomaterials Congress, Berlin 623 (1992).

Zhao, Y., et al., "Effect of Irradiation on Crystallinity and Mechanical Properties of Ultrahigh Molecular Weight Polyethylene", *J. Appl. Polym. Sci.,* 50:1797 (1993).

News You Can Use, vol. II, No. 2 (May 1996).

"For the Tough Jobs: 1900 UHMW Polymer", Himont Inc.(1988).

"Abrasion–Resistant 1900 UHMW Polymer", Hercules Inc. (1979).

"Technical Information: 1900 Ultrahigh Molecular Weight Polymer, General Information and Applications", Bulletin HPE–101A, Hercules U.S.A., Inc. (1989).

"Technical Information: 1900 Ultrahigh Molecular Weight Polymer, Nuclear Radiation Effects", Bulletin HPE–111, Himont U.S.A. Inc. (1985).

"Techinical Information: 1900 Ultrahigh Molecular Weight Polymer, Effect of Polymer Modification", Bulletin HPE–116, Himont U.S.A.. Inc. (1987).

\* cited by examiner

CHEMICALLY CROSSLINKED ULTRAHIGH MOLECULAR WEIGHT POLYETHYLENE FOR ARTIFICIAL HUMAN JOINTS

This is a continuation of U.S. patent application Ser. No. 08/698,638, filed Aug. 15, 1996 now abandoned, entitled "Chemically Crosslinked Ultrahigh Molecular Weight Polyethylene for Artificial Human Joints," which is a divisional application of United States patent application Ser. No. 08/376,953 filed on Jan. 20, 1995, of the same title, now abandoned. The entire disclosure of the prior application Ser. No. 08/376,953, from which a copy of the oath or declaration is supplied herewith, is considered to be part of the disclosure of this pending patent application and is hereby incorporated by reference herein.

TECHNICAL FIELD OF THE INVENTION

The present invention relates to polymers. It discloses a method for enhancing the wear-resistance of polymers, especially polymers that are to be irradiated, by crosslinking the polymers. The crosslinked polymers may be annealed to stabilize their size shrinkage. The polymers disclosed herein are particularly useful for making in vivo implants.

BACKGROUND OF THE INVENTION

Ultrahigh molecular weight polyethylene (hereinafter referred to as "UHMW polyethylene") is commonly used to make prosthetic joints such as artificial hip joints. In recent years, it has become increasingly apparent that tissue necrosis and interface osteolysis, in response to UHMW polyethylene wear debris, are primary contributors to the long-term loosening failure of prosthetic joints. For example, the process of wear of acetabular cups of UHMW polyethylene in artificial hip joints introduces many microscopic wear particles into the surrounding tissues. The reaction of the body to these particles includes inflammation and deterioration of the tissues, particularly the bone to which the prosthesis is anchored. Eventually, the prosthesis becomes painfully loose and must be revised. It is generally accepted by orthopaedic surgeons and biomaterials scientists that the reaction of tissue to wear debris is the chief cause of long-term failure of such prostheses.

Laboratory experiments and examination of worn polyethylene components, as used in acetabular cups of total hip prostheses, after removal from patients, have shown that polyethylene wear in vivo primarily involves three fundamental mechanisms: adhesive, abrasive, and fatigue wear {Brown, K. J., et al., *Plastics in Medicine & Surgery Plastics & Rubber Institute*, London, 2.1–2.5 (1975); Nusbaum, H. J. & Rose, R. M., *J. Biomed. Materials Res.*, 13:557–576 (1979); Rostoker, W., et al., *J. Biomed. Materials Res.*, 12:317–335 (1978); Swanson, S. A. V. & Freeman, M. A. R., Chapter 3, "Friction, lubrication and wear.", *The Scientific Basis of Joint Replacement*, Pittman Medical Publishing Co., Ltd. (1977).}

Adhesive wear occurs when there is local bonding between asperities on the polymer and the opposing (metal or ceramic) counterface. If the ratio of the strength of the adhesive bond to the cohesive strength of the polymer is great enough, the polymer may be pulled into a fibril, finally breaking loose to form a wear particle. Small wear particles (measuring microns or less) are typically produced.

Abrasive wear occurs when asperities on the surface of the femoral ball, or entrapped third-body particles, penetrate into the softer polyethylene and cut or plow along the surface during sliding. Debris may be immediately formed by a cutting process, or material may be pushed to the side of the track by plastic deformation, but remain an integral part of the surface.

Fatigue wear is dependent on cyclic stresses applied to the polymer. As used herein, fatigue wear is an independent wear mechanism involving crack formation and propagation within the polymer. Cracks may form at the surface and coalesce, releasing wear particles as large as several millimeters and leaving behind a corresponding pit on the surface, or cracks may form a distance below the surface and travel parallel to it, eventually causing sloughing off of large parts of the surface.

There are gaps in the prior art regarding the contributions of the above three basic mechanisms to the wear of polyethylene cups in vivo. While numerous laboratory studies and analyses of retrieved implants have provided valuable details on wear in vivo, there is ongoing disagreement regarding which wear mechanisms predominate and what are the controlling factors for wear.

However, it is clear that improving the wear resistance of the UHMW polyethylene socket and, thereby, reducing the amount of wear debris generated each year, would extend the useful life of artificial joints and permit them to be used successfully in younger patients. Consequently, numerous modifications in physical properties of UHMW polyethylene have been proposed to improve its wear resistance.

UHMW polyethylene components are known to undergo a spontaneous, post-fabrication increase in crystallinity and changes in other physical properties. {Grood, E. S., et al., *J. Biomedical Materials Res.*, 16:399–405 (1976); Kurth, J., et al., Trans. Third World Biomaterials Congress, 589 (1988); Rimnac, C. M., et al., *J. Bone & Joint Surgery*, 76-A(7):1052–1056 (1994)}. These occur even in stored (non-implanted) cups after sterilization with gamma radiation which initiates an ongoing process of chain scission, crosslinking, and oxidation or peroxidation involving free radical formation. {Eyerer, P. & Ke, Y. C., *J. Biomed. Materials Res.* 18:1137–1151 (1984); Nusbaum, H. J. & Rose, R. M., *J. Biomed. Materials Res.*, 13:557–576 (1979); Roe, R. J., et al., *J. Biomed. Materials Res.*, 15:209–230 (1981); Shen, C. & Dumbleton, J. H., *Wear*, 30:349–364 (1974)}. These degradative changes may be accelerated by oxidative attack from the joint fluid and cyclic stresses applied during use. {Eyerer, P. & Ke, Y. C., *J. Biomed. Materials Res.*, supra; Grood, E. S., et al., *J. Biomed. Materials Res.*, supra; Rimnac, C. M., et al., ASTM Symposium on Biomaterials' Mechanical Properties, Pittsburgh, May 5–6 (1992)}.

On the other hand, it has been reported that the best total hip prosthesis for withstanding wear is one with an alumina head and an irradiated UHMW polyethylene socket, as compared to a un-irradiated socket. The irradiated socket had been irradiated with $10^8$ rad of $\gamma$-radiation, or about 40 times the usual sterilization dose. {Oonishi, H., et al., *Radiat. Phys. Chem.*, 39(6):495–504 (1992)). The usual average sterilization dose ranges from 2.5 to 4.0 Mrad. Other investigators did not find any significant reduction in the wear rates of UHMW polyethylene acetabular cups which had been irradiated, in the solid phase, in special atmospheres to reduce oxidation and encourage crosslinking. {Ferris, B. D., *J. Exp. Path.*, 71:367–373 (1990); Kurth, M., et al., Trans. Third World Biomaterials Congress, 589 (1988); Roe, R. J., et al., *J. Biomed. Materials Res.*, 15:209–230 (1981); Rose, et al., *J. Bone & Joint Surgery*, 62A (4):537–549 (1980); Streicher, R. M., *Plastics & Rubber Processing & Applications*, 10:221–229 (1988)}.

Meanwhile, DePuy.DuPont Orthopaedics has fabricated acetabular cups from conventionally extruded bar stock that has previously been subjected to heating and hydrostatic pressure that reduces fusion defects and increases the crystallinity, density, stiffness, hardness, yield strength, and resistance to creep, oxidation and fatigue. (U.S. Pat. No. 5,037,928, to Li, et al., Aug. 6, 1991; Huang, D. D. & Li, S., Trans. 38th Ann. Mtg., *Orthop. Res. Soc.*, 17:403 (1992); Li, S. & Howard, E. G., Trans. 16th Ann. Society for Biomaterials Meeting, Charleston, S.C., 190 (1990).} Silane crosslinked UHMW polyethylene (XLP) has also been used to make acetabular cups for total hip replacements in goats. In this case, the number of in vivo debris particles appeared to be greater for XLP than conventional UHMW polyethylene cup implants {Ferris, B. D., *J. Exp. Path.*, 71:367–373 (1990)}.

Other modifications of UHMW polyethylene have included: (a) reinforcement with carbon fibers {"Poly Two Carbon-Polyethylene Composite-A Carbon Fiber Reinforced Molded Ultra-High Molecular Weight Polyethylene", Technical Report, Zimmer (a Bristol-Myers Squibb Company), Warsaw (1977)}; and (b) post processing treatments such as solid phase compression molding {Eyerer, P., Polyethylene, *Concise Encyclopedia of Medical & Dental Implant Materials*, Pergamon Press, Oxford, 271–280 (1990); Li, S., et al., *Trans. 16th Annual Society for Biomaterials Meeting*, Charleston, S.C., 190 (1990); Seedhom, B. B., et al., *Wear*, 24:35–51 (1973); Zachariades, A. E., Trans. Fourth World Biomaterials Congress, 623 (1992)}. However, to date, none of these modifications has been demonstrated to provide a significant reduction in the wear rates of acetabular cups. Indeed, carbon fiber reinforced polyethylene and a heat-pressed polyethylene have shown relatively poor wear resistance when used as the tibial components of total knee prosthesis. {Bartel, D. L., et al.,*J. Bone & Joint Surgery*, 68-A(7):1041–1051 (1986); Conelly, G. M., et al.,*J. Orthop. Res.*, 2:119–125 (1984); Wright, T. M., et al., *J. Biomed. Materials Res.*, 15: 719–730 (1981); Bloebaum, R. D., et al., *Clin. Orthop.*, 269:120–127 (1991); Goodman, S. & Lidgren, L., *Acta Orthop. Scand.*, 63(3) 358–364 (1992); Landy, M. M. & Walker, P. S., *J. Arthroplasty*, Supplement, 3:S73–S85 (1988); Rimnac, C. M., et al., *Trans. Orthopaedic Research Society*, 17:330 (1992); Rimnac, C. M. et al., "Chemical and mechanical degradation of UHMW polyethylene: Preliminary report of an in vitro investigation," ASTM Symposium on Biomaterials' Mechanical Properties, Pittsburgh, May 5–6 (1992)}.

SUMMARY OF THE INVENTION

One aspect of the invention presents a method for reducing the crystallinity of a polymer so that it can better withstand wear. An effective method for reducing the crystallinity of the polymer is by crosslinking. For reduction of crystallinity, the polymer may be irradiated in the melt or, preferably, chemically crosslinked in the molten state. The method is particularly useful for polymer which undergoes irradiation sterilization in the solid state. It is advantageous if the crosslinked polymer is annealed to stabilize its shrinkage.

Another aspect of the invention presents a method for making in vivo implants based on the above treatment of the polymer.

Another aspect of the invention presents a polymer, made from the above method, having an increased ability to withstand wear.

Another aspect of the invention presents in vivo implants made from the polymer described above.

DETAILED DESCRIPTION OF THE INVENTION

Figure 1A:
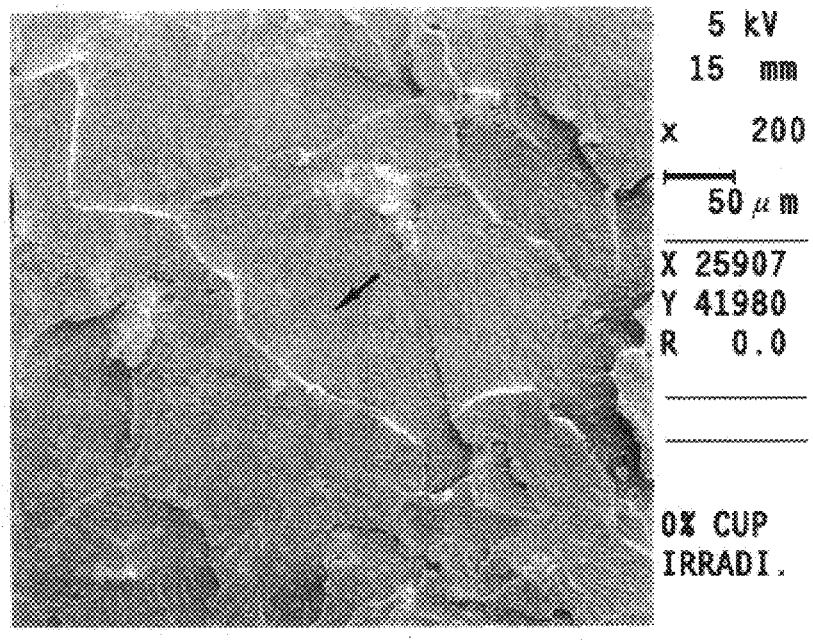
FIG. 1 presents SEM micrographs of fracture surfaces of the compression molded UHMW polyethylene (after irradiation) at magnifications of (A)×200 and (B)×5000.

Abbreviations used in this application are as follows:

DSC—differential scanning calorimetry.

FTIR—Fourier Transform Infrared Spectroscopy

SEM—scanning electron microscopy

UHMW—ultra-high molecular weight

UHMWPE—ultra-high molecular weight polyethylene, also referred to as UHMW polyethylene WAXS—wide angle X-ray scattering Cutting through the plethora of choices and confusion in the art, applicants discovered that a low degree of crystallinity is a major factor in increasing the ability of polyethylene to withstand wear in vivo, contrary to the above teaching of DePuy.DuPont Orthopaedics. Solid polymers that can crystallize generally contain both crystalline and amorphous states. These two states have different physical properties. The applicants believe that the crystalline component of polymers is more brittle and less wear-resistant than the amorphous component, the amorphous component being more ductile and more wear-resistant.

In the present invention, the degree of crystallinity of the polymer is preferably reduced by crosslinking. The crosslinking can be achieved by various methods known in the art, for example, by irradiation crosslinking of the molten polymer; photocrosslinking of the molten polymer; and crosslinking of the polymer with a free radical generating chemical. The preferred method is chemical crosslinking. As indicated, if the crosslinking is to be achieved by irradiation, the polymer should be irradiated in the melt, unlike the above mentioned prior art irradiation methods, such as in Oonishi et al. Applicants also discovered that such a crosslinked polymer is useful for in vivo implant because it is wear resistant. Such in vivo implant has not been envisioned by the prior art. Moreover, since acetabular cups are routinely sterilized by irradiation which increases the crystallinity of UHMW polyethylene {Bhateja, S. K., *J. Macromol. Sci. Phys.*, B22:159 (1983); Bhateja, S. K., et al., *J. Polym. Sci., Polym. Phys. Ed.*, 21:523 (1983); and Bhateja, S. K. & Andrews, E. H., *J. Mater. Sci.*, 20:2839 (1985)}, applicants realized that the irradiation in fact makes the polymer more susceptible to wear, contrary to the teaching of the prior art such as Oonishi et al, supra. By crosslinking the polymer before sterilization by irradiation, applicants' method mitigates the deleterious effects of irradiation, such as chain scission. Applicants' method calls for determination of the crystallinity after irradiation to adjust the crosslinking conditions to reduce crystallinity. The polymer may also be irradiated under certain conditions e.g., in nitrogen atmosphere to reduce the immediate and subsequent amounts of oxidation. Reducing oxidation increases the amount of crosslinking. In producing acetabular cups, applicants discovered that both uncrosslinked and crosslinked cups show shrinkage in size, but crosslinked cups tend to shrink more than uncrosslinked cups. Thus, the present invention also provides for annealing the crosslinked polymer in order to shrink it to a stable size before reshaping the polymer.

Most importantly, implants which are produced by the foregoing methods of the invention are more wear resistant than conventional untreated polymer. Thus, an example of the present invention presents an UHMW polyethylene acetabular cup of a total hip prosthesis which has been chemically crosslinked by a peroxide, and then sterilized by irradiation, showing only one fifth of the wear of a control cup after a simulated year of in vivo use.

Method for Treating the Polymers

One aspect of the invention presents a method for treating a polymer to reduce its crystallinity to less than 45% to enable the resulting polymer to better withstand wear. The polymer's crystallinity is preferably reduced by crosslinking in the molten state followed by cooling to the solid state. Preferably, the crosslinking reduces the crystallinity of the polymer by about 10% to 50%; more preferably, by about 10% to 40%; and most preferably, by about 10% to 30% compared to an uncrosslinked polymer. For example, the preferable degree of crystallinity of crosslinked UHMW polyethylene is between about 24% to 44%; more preferably, between 29% to 44%; and most preferably, between about 34% to 44% After sterilization by irradiation, the crosslinked polymer has a reduced crystallinity compared to the uncrosslinked polymer. Preferably, the irradiated crosslinked polymer possesses about 10% to 50%; more preferably, about 10% to 40%; and most preferably, about 10% to 30% less degree of crystallinity compared to the uncrosslinked but irradiated polymer. For example, the preferable degree of crystallinity of irradiated, crosslinked UHMW polyethylene is between about 28% to 51%; more preferably, between about 33% to 51%; and most preferably, between about 39% to 51%. For example, EXAMPLE 1, Table 1 below shows the degree of crystallinity for UHMW polyethylene containing different weight percentage of peroxide. In the following EXAMPLE 2, UHMW polyethylene which was crosslinked by 1% weight (wt) peroxide exhibited about 39.8% crystallinity, i.e. about a 19% reduction in crystallinity compared to uncrosslinked UHMW polyethylene which possessed about 49.2% crystallinity. After gamma irradiation to an average dose of about 3.4 Mrad, the crosslinked UHMW polyethylene exhibits about 42% crystallinity, i.e., a reduction of about 25% in crystallinity compared to the originally uncrosslinked but radiation sterilized UHMW polyethylene which possessed about 55.8% crystallinity. Thus, it is contemplated that after the usual sterilization dosage in the solid state, which generally averages between 2.5 to 4.0 Mrad, the treated polymer preferably possesses less than about 45% crystallinity, and more preferably about 42% crystallinity or less. Also, the treated polymer preferably possesses less than about 43%, more preferably less than about 40%, crystallinity before irradiation in the solid state.

If the polymer is to be molded, e.g. as an acetabular cup, the polymer may be placed in the mold and crosslinked therein. Further crosslinking examples are: (1) irradiation of the polymer when it is in a molten state, e.g. UHMW polyethylene has been crosslinked in the melt by electron beam irradiation; and molten linear polyethylene has been irradiated with fast electrons {Dijkstra, D. J. et al., *Polymer*, 30:866–709 (1989); Gielenz G. & Jungnickle, B. J., *Colloid & Polymer Sci.*, 260:742–753 (1982)}; the polymer may also be gamma-irradiated in the melt; and (2) photocrosslinking of the polymer in the melt, e.g. polyethylene and low-density polyethylene have been photocrosslinked {Chen, Y. L. & Ranby, B., *J. Polymer Sci.: Part A: Polymer Chemistry*, 27:4051–4075, 4077–4086 (1989)}; Qu, B. J. & Ranby, B., *J. Applied Polymer Sci.*, 48:711–719 (1993)}.

Choices of Polymers

The polymers are generally polyhydrocarbons. Ductile polymers that wear well are preferred. Examples of such polymers include: polyethylene, polypropylene, polyester and polycarbonates. For example, UHMW polymers may be used, such as UHMW polyethylene and UHMW polypropylene. An UHMW polymer is a polymer having a molecular weight (MW) of at least about a million.

For in vivo implants, the preferred polymers are those that are wear resistant and have exceptional chemical resistance. UHMW polyethylene is the most preferred polymer as it is known for these properties and is currently widely used to make acetabular cups for total hip prostheses. Examples of UHMW polyethylene are: Hostalen GUR 415 medical grade UHMW polyethylene flake (Hoechst-Celanese Corporation, League City, Tex.), with a weight average molecular weight of $6 \times 10^6$ MW; Hostalen GUR 412 with a weight average molecular weight of between $2.5 \times 10^6$ to $3 \times 10^6$ MW; Hostalen GUR 413 of $3 \times 10^6$ to $4 \times 10^6$ MW; RCH 1000 (Hoechst-Celanese Corp.); and HiFax 1900 of $4 \times 10^6$ MW (HiMont, Elkton, Md.). GUR 412, 413 and 415 are in the form of powder. RCH 1000 is usually available as compression molded bars. Historically, companies which make implants have used GUR 412 and GUR 415 for making acetabular cups. Recently, Hoechst-Celanese Corp. changed the designation of GUR 415 to 4150 resin and indicated that 4150 HP was for use in medical implants.

Methods for Characterizing the Polymers
(Especially the Determination of Their Crystallinity)

The degree of crystallinity of the crosslinked polymer may be determined after it has been crosslinked or molded. In case the treated polymer is further irradiated, e.g., to sterilize the polymer before its implant into humans, the degree of crystallinity may be determined after irradiation, since irradiation effects further crystallization of the polymer.

The degree of crystallinity can be determined using methods known in the art, e.g. by differential scanning calorimetry (DSC), which is generally used to assess the crystallinity and melting behavior of a polymer. Wang, X. & Salovey, R., *J. App. Polymer Sci.*, 34: 593–599 (1987).

X-ray scattering from the resulting polymer can also be used to further confirm the degree of crystallinity of the polymer, e.g. as described in Spruiell, J. E., & Clark, E. S.,in "Methods of Experimental Physics", L. Marton & C. Marton, Eds., Vol. 16, Part B, Academic Press, New York (1980). Swelling is generally used to characterize crosslink distributions in polymers, the procedure is described in Ding, Z. Y., et al., *J. Polymer Sci., Polymer Chem.*, 29: 1035–38 (1990). Another method for determining the degree of crystallinity of the resulting polymer may include FTIR {Painter, P. C. et al., "The Theory Of Vibrational Spectroscopy And Its Application To Polymeric Materials", John Wiley and Sons, New York, U.S.A. (1982)} and electron diffraction. FTIR assesses the depth profiles of oxidation as well as other chemical changes such as unsaturation {Nagy, E. V., & Li, S., "A Fourier transform infrared technique for the evaluation of polyethylene orthopaedic bearing materials", Trans. Soc. for Biomaterials, 13:109 (1990); Shinde, A. & Salovey, R., *J. Polymer Sci., Polym. Phys. Ed.*, 23:1681–1689 (1985)}. A further method for determining the degree of crystallinity of the resulting polymer may include density measurement according to ASTM D1505-68.

Methods for Chemically Crosslinking the Polymers

The polymer is preferably chemically crosslinked to decrease its crystallinity. Preferably, the crosslinking chemical, i.e. a free radical generating chemical, has a long half-life at the molding temperature of the chosen polymer. The molding temperature is the temperature at which the polymer is molded. The molding temperature is generally at or above the melting temperature of polymer. If the crosslinking chemical has a long half-life at the molding temperature, it will decompose slowly, and the resulting free radicals can diffuse in the polymer to form a homogeneous crosslinked network at the molding temperature. Thus, the molding temperature is also preferably high enough to allow the flow of the polymer to occur to distribute or diffuse the crosslinking chemical and the resulting free radicals to form the homogeneous network. For UHMW polyethylene, the molding temperature is between 150° to 220° C. and the molding time is between 1 to 3 hours; the preferable molding temperature and time being 170° C. and 2 hours, respectively.

Thus, the crosslinking chemical may be any chemical that decomposes at the molding temperature to form highly reactive intermediates, free radicals, which would react with the polymers to form the crosslinked network. Examples of free radical generating chemicals are peroxides, peresters, azo compounds, disulfides, dimethacrylates, tetrazenes, and divinyl benzene. Examples of azo compounds are: azobisisobutyronitride, azobis-isobutyronitrile, and dimethylazodi isobutyrate. Examples of peresters are t-butyl peracetate and t-butyl perbenzoate.

Preferably the polymer is crosslinked by treating it with an organic peroxide. The preferable peroxides are 2,5-dimethyl-2,5-bis(tert-butylperoxy)-3-hexyne (Lupersol 130, Atochem Inc., Philadelphia, Pa.); 2,5-dimethyl-2,5-di-(t-butylperoxy)-hexane; t-butyl α-cumyl peroxide; di-butyl peroxide; t-butyl hydroperoxide; benzoyl peroxide; dichlorobenzoyl peroxide; dicumyl peroxide; di-tertiary butyl peroxide; 2,5 dimethyl-2,5 di(peroxy benzoate) hexyne-3; 1,3-bis(t-butyl peroxy isopropyl) benzene; lauroyl peroxide; di-t-amyl peroxide; 1,1-di-(t-butylperoxy) cyclohexane; 2,2-di-(t-butylperoxy)butane; and 2,2-di-(t-amylperoxy) propane. The more preferred peroxide is 2,5-dimethyl-2,5-bis(tert-butylperoxy)-3-hexyne. The preferred peroxides have a half-life of between 2 minutes to 1 hour; and more preferably, the half-life is between 5 minutes to 50 minutes at the molding temperature.

Generally, between 0.2 to 5.0 wt % of peroxide is used; more preferably, the range is between 0.5 to 3.0 wt % of peroxide; and most preferably, the range is between 0.6 to 2 wt %.

The peroxide can be dissolved in an inert solvent before being added to the polymer powder. The inert solvent preferably evaporates before the polymer is molded. Examples of such inert solvents are alcohol and acetone.

For convenience, the reaction between the polymer and the crosslinking chemical, such as peroxide, can generally be carried out at molding pressures. Generally, the reactants are incubated at molding temperature, between 1 to 3 hours, and more preferably, for about 2 hours.

The reaction mixture is preferably slowly heated to achieve the molding temperature. After the incubation period, the crosslinked polymer is preferably slowly cooled down to room temperature. For example, the polymer may be left at room temperature and allowed to cool on its own. Slow cooling allows the formation of a stable crystalline structure.

The reaction parameters for crosslinking polymers with peroxide, and the choices of peroxides, can be determined by one skilled in the art. For example, a wide variety of peroxides are available for reaction with polyolefins, and investigations of their relative efficiencies have been reported {Lem, K. W. & Han, C. D., *J. Appl. Polym. Sci.*, 27:1367 (1982); Kampouris, E. M. & Andreopoulos, A. G., *J. Appl. Polym. Sci.*, 34:1209 (1987) and Bremner, T. & Rudin, A. *J. Appl. Polym. Sci.*, 49:785 (1993)}. Differences in decomposition rates are perhaps the main factor in selecting a particular peroxide for an intended application {Bremner, T. & Rudin, A. *J. Appl. Polym. Sci.*, 49:785 (1993)}. Bremner and Rudin, id., compared three dialkyl peroxides on the basis of their ability to increase the gel content, crosslinking efficiency, and storage modulus of virgin polyethylene through a crosslinking mechanism and found that they decreased in the order of α,α-bis(tertiary butylperoxy)-p-diisopropyl benzene>dicumyl peroxide>2,5-dimethyl-2,5-di-(tertiary butylperoxy)-hexyne-3 at the same active peroxide radical concentrations and temperature.

More specifically, peroxide crosslinking of UHMW polyethylene has also been reported {de Boer, J. & Pennings, A. J., *Makromol. Chem. Rapid Commun.*, 2:749 (1981); de Boer, J. & Pennings, A. J., *Polymer*, 23:1944 (1982); de Boer, J., et al., *Polymer*, 25:513 (1984) and Narkis, M., et al., *J. Macromol. Sci. Phys.*, B 26:37, 58 (1987)}. de Boer et al. crosslinked UHMW polyethylene in the melt at 180° C. by means of 2,5-dimethyl-2,5-di-(tert-butylperoxy)-hexyne-3 and found that crosslinks and entanglements, whether trapped or not, contributed to the same degree to the decrease in crystallinity of UHMW polyethylene upon crosslinking (de Boer, J. & Pennings, A. J., *Polymer*, 23:1944 (1982)). It was concluded that an almost completely crosslinked (or gelled) material with high crystallinity and good mechanical properties could be obtained by using as little as 0.2–0.3 wt % of peroxide.

Some of the above references investigated the effect of peroxide crosslinking on UHMW polyethylene, such as in lowering crystallinity; and the effects of reaction parameters, such as peroxide concentrations {de Boer, J. & Pennings, A. J., *Polymer*, 23:1944 (1982); Narkis, M., et al., *J. Macromol. Sci. Phys.*, B 26:37–58 (1987)}. However, these references do not address the effect of peroxide crosslinking or the lowering of crystallinity in relation to the wear property of the resulting polymer. For example, de Boer and Pennings, in *Polymer*, 23:1944 (1982), were concerned with the effect of crosslinking on the crystallization behavior and the tensile properties of UHMW polyethylene. The authors found that tensile properties, such as tensile strength at break point and Young's modulus, of the UHMW polyethylene, showed a tendency to decrease with increasing peroxide content.

Similarly, Narkis, M., et al., *J. Macromol. Sci. Phys.*, B 26:37–58 (1987), separately determined the effects of irradiation and peroxide on the crosslinking and degree of crystallinity of UHMW polyethylene (Hostalen GUR 412), high molecular weight polyethylene, and normal molecular weight polyethylene. However, M. Narkis et al., did not study the inter-relationship of peroxide crosslinking and irradiation, nor their effects on wear resistance.

Use of Crosslinked Polymers for In Vivo Implants

Another aspect of the invention presents a process for making in vivo implants using the above chemically crosslinked polymer. Since in vivo implants are often irradiated to sterilize them before implant, the present invention provides the further step of selecting for implant use, a polymer with about 45% crystallinity or less after irradiation sterilization. For γ-irradiation sterilization, the minimum dosage is generally 2.5 Mrad. The sterilization dosage generally falls between 2.5 and 4.0 Mrad. The preferable degree of crystallinity is between 25% to 45% crystallinity. In EXAMPLE 2 below, the polymer has about 39.8% crystallinity after crosslinking; and about 42% crystallinity after further irradiation with γ-radiation to an average dose of about 3.4 Mrad. Thus, the chemically crosslinked UHMW polymer preferably possesses less than about 43% crystallinity before irradiation in the solid state, and less than about 45% crystallinity after irradiation with γ-radiation to an average dose of about 3.4 Mrad.

Annealing of Crosslinked Polymers

Applicants observed that both crosslinked and uncrosslinked polymers tended to shrink, but the crosslinked polymer tended to shrink more than the uncrosslinked polymer (see EXAMPLE 3 below). Thus, the present invention further provides for annealing a polymer to pre-shrink it to a size which will not shrink further (i.e. stabilize the polymer's shrinkage or size). Thus, one aspect of the invention provides for a method of: 1) crosslinking a polymer, 2) selecting a crosslinked polymer of reduced crystallinity, 3) annealing the polymer to stabilize its size. Thus, the polymer can be molded at a size larger than desired, and the molded polymer is then annealed to stabilize its size. After size stabilization, the molded polymer is then resized, such as by machining, into a product with the desired dimension.

The annealing temperature is preferably chosen to avoid thermal oxidation of the crosslinked polymer which will increase its crystallinity. Thus, the annealing temperature is preferably below the melting point of the molded polymer before irradiation. For example, the melting temperatures of molded UHMW polyethylene and molded 1 wt % peroxide UHMW polyethylene are 132.6° C. and 122.3° C., before irradiation, respectively. The preferable annealing temperature for both these molded UHMW polyethylenes is between 60° C. to 120° C., before irradiation, and more preferably 100° C. These temperatures were determined by observation, based on experiments, of their minimal effect on thermal oxidation of the molded polymers. The annealing time is generally between 1 to 6 hours, and more preferably between 2 to 4 hours. In the case of UHMW polyethylene, the annealing time is preferably between 2 to 4 hours, and more preferably about 2 hours.

To further avoid thermal oxidation of the crosslinked polymer, the annealing is most preferably conducted in a vacuum oven.

To ensure that the crosslinked and annealed polymer has the desired degree of crystallinity, its degree of crystallinity is preferably determined after the annealing process, using the method(s) described previously.

Wear-Resistant Polymers

Another aspect of the invention presents a polymer with 45% of crystallinity or less, in particular, after irradiation in the solid state and/or annealing. In EXAMPLE 2 below, the polymer has about 39.8% crystallinity after crosslinking; and about 42% crystallinity, after further irradiation with γ-radiation to an average dose of about 3.4 Mrad; or about 40.8% crystallinity, after crosslinking and annealing, but before irradiation in the solid state.

The polymers of the present invention can be used in any situation where a polymer, especially UHMW polyethylene, is called for, but especially in situations where high wear resistance is desired and irradiation of the solid polymer is called for. More particularly, these polymers are useful for making in vivo implants.

In Vivo Implants Made of Crosslinked Polymers

An important aspect of this invention presents in vivo implants that are made with the above polymers or according to the method presented herein. These implants are more wear resistant than their untreated counterpart, especially after irradiation. In particular, these in vivo implants are chemically crosslinked UHMW polymers, which have been molded, annealed, and resized into the shape of the implants. Further, the chemically crosslinked UHMW polymer preferably possesses less than about 43% crystallinity before irradiation in the solid state, and less than about 45% crystallinity, after γ-irradiation to an average dose of 3.4 Mrad, in the solid state. The modified polymer can be used to make in vivo implants for various parts of the body, such as components of a joint in the body. For example, in the hip joints, the modified polymer can be used to make the acetabular cup, or the insert or liner of the cup, or trunnion bearings (e.g. between the modular head and the stem). In the knee joint, the modified polymer can be used to make the tibial plateau (femoro-tibial articulation), the patellar button (patello-femoral articulation), and trunnion or other bearing components, depending on the design of the artificial knee joint. In the ankle joint, the modified polymer can be used to make the talar surface (tibio-talar articulation) and other bearing components. In the elbow joint, the modified polymer can be used to make the radio-humeral joint, ulno-humeral joint, and other bearing components. In the shoulder joint, the modified polymer can be used to make the glenoro-humeral articulation, and other bearing components. In the spine, the modified polymer can be used to make intervertebral disk replacement and facet joint replacement. The modified polymer can also be made into temporo-mandibular joint (jaw) and finger joints. The above are by way of example, and are not meant to be limiting.

Having described what the applicants believe their invention to be, the following examples are presented to illustrate the invention, and are not to be construed as limiting the scope of the invention.

EXAMPLES

Example 1

Experimental Details

Commercial-grade UHMW polyethylene GUR 415 (from Hoechst-Celanese Corporation, League City, Tex.), with a weight average molecular weight of $6 \times 10^6$, was used as received. The peroxide used was 2,5-dimethyl-2,5-bis(tert-butylperoxy)-3-hexyne (Lupersol 130, Atochem Inc., Philadelphia, Pa.). The reason for choosing Lupersol 130 was its long half-life at elevated temperature. The peroxide will decompose slowly, and the resultant free radicals can diffuse in the specimen to form a homogeneous network at elevated temperatures.

Mixing of the UHMW polyethylene and the peroxide was accomplished by dispersing polyethylene powder in an acetone solution of the peroxide and subsequently evaporating the solvent (de Boer, J., et al., *J. Polym. Sci., Polym. Phys. Ed.*, 14:187 (1976); de Boer, J. & Pennings, A. J., *Makromol. Chem, Rapid Commun.*, 2:749 (1981) and de Boer, J. & Pennings, A. J., *Polymer*, 23:1944 (1982)). The mixed powder (22 g) was poured into the mold cavity and then compression molded in a mold between two stainless-steel plates at 120° C. and ram pressure 11×10$^3$ kPa for 10 minutes in order to evacuate the trapped air in the powder. After pressing, the pressure was reduced to 7.5×10$^3$ kPa and the specimen was heated to 170° C. by circulated heating oil. These conditions were held for 2 hours. The half-life time of peroxide at 170° C. in dodecane is about 9 minutes. After 2 hours, pressure was increased to 15×10$^3$ kPa to avoid cavities in the specimen and sink marks on the surface and the specimen was slowly cooled in the mold to room temperature. The mold was in the shape of an acetabular cup for a total hip prosthesis.

The specimens were irradiated with γ-rays at room temperature in air atmosphere by SteriGenics International (Tustin, Calif.). Cobalt-60 was used as a source of gamma irradiation. The radiation doses were delivered at a dose rate of 5 kGy/hr. Specimens received doses to an average of about 34 kGy (i.e., an average of about 3.4 Mrad).

The physical properties of specimens before and after irradiation were characterized by DSC, equilibrium swelling, FTIR, and WAXS measurements. Surface morphology was examined by SEM.

Results and Discussion

Before irradiation, the degree of crystallinity, peak melting temperature, and recrystallization temperature for the peroxide-free specimen are 49.2%, 132.6 and 115.5° C., respectively. For a 1 wt % peroxide specimen, the degree of crystallinity, peak melting temperature, and recrystallization temperature are reduced to 39.8%, 122.3 and 110.1° C., respectively. Peroxide crosslinking reactions are accompanied by the decomposition of peroxide and abstraction of hydrogen atoms, and the resulting combination of alkyl radicals to produce carbon-carbon crosslinks. Generally, this reaction was performed above the melting temperature of the polymer. Thus the crosslinking step preceded the crystallization step. It was suggested that crystallization from a crosslinked melt produced an imperfect crystal, and crosslinks suppressed crystal growth, resulting in the depression of melting temperature and a decreased crystallinity (decreased crystallite size) {de Boer, J. et al., *J. Polym. Sci., Polym. Phys. Ed.*, 14:187 (1976); de Boer, J. & Pennings, A. J., *Makromol. Chem. Rapid Commun.*, 2:749 (1981); de Boer, J. & Pennings, A. J., *Polymer*, 23:1944 (1982) and Narkis, M., et al., *J. Macromol. Sci. Phys.*, B26:37 (1987)}. Wide-angle x-ray scattering shows that the degree of crystallinity, crystal perfection and size decrease after peroxide crosslinking. For swelling measurement, the peroxide-free specimen dissolves completely in boiling p-xylene. The gel content, degree of swelling, and average molecular weight between crosslinks for the 1 wt % peroxide specimen are 99.6%, 2.53, and 1322 (g/mol), respectively. Because of the extremely long polymer chains in UHMW polyethylene, only a few crosslinks were needed for gelation. In addition, an almost 100% gel can be obtained by peroxide crosslinking because no chain scission occurs by peroxide crosslinking.

After irradiation, the degree of crystallinity and peak melting temperature for the peroxide-free specimen were increased to 55.8% and 135° C., respectively. It was suggested that irradiation-induced scission of taut tie molecules permits recrystallization of broken chains from the noncrystalline regions, and results in an increase in the degree of crystallinity and an increased perfection of existing folded chain crystallites {Narkis, M., et al., *J. Macromol. Sci. Phys.*, B26:37 (1987); Bhateja, S. K., *J. Macromol. Sci. Phys.*, B22:159 (1983); Bhateja, S. K., et al., *J. Polym. Sci., Polym. Phys. Ed.*, 21:523 (1983); Kamel, I. & Finegold, L., *J. Polym. Sci., Polym. Phys. Ed.*, 23:2407 (1985); Shinde, A. & Salovey, R., *J. Polym. Sci., Polym. Phys. Ed.*, 23:1681 (1985); Bhateja, S. K. & Andrews, E. H., *J. Mater. Sci.*, 20:2839 (1985); Minkova, L., *Colloid Polym. Sci.*, 266:6 (1988); Minkova, L. & Mihailov, M., *Colloid Polym. Sci.*, 268:1018 (1990) and Zhao, Y., et al., *J. Appl. Polym. Sci.*, 50:1797 (1993)}. The gel content after irradiation for the peroxide-free specimen was 70.8%.

For the 1 wt % peroxide specimen, the degree of crystallinity and peak melting temperature after irradiation were increased to 42% (about 2% increase) and 125.1° C., respectively. The gel content decreased to 97.5% after irradiation, whereas, the degree of swelling and molecular weight between crosslinks increased to 3.35 and 2782 (g/mol), respectively. Apparently, irradiation-induced scission of taut tie molecules resulted in a decreased gel content and an increased degree of swelling. However, after peroxide crosslinking, the effect of irradiation on network properties was mitigated. As a result of peroxide crosslinking, radiation-induced chain scission becomes less important in determining gel content. We suggest that peroxide crosslinking reduces the effect of irradiation on the crosslinked network because crosslinks introduced by peroxide crosslinking stabilize chain fragments resulting from the scission of taut tie molecules and suppress recrystallization of broken chains. Wide-angle x-ray scattering showed that crystal perfection increased after irradiation. It is suggested that crystal perfection was improved by irradiation-induced scission of taut tie molecules in the amorphous regions.

FTIR measurements showed that, after irradiation, the carbonyl concentration significantly increased. This is because the free radicals produced by irradiation reacted with oxygen dissolved and/or diffused in the polymer. In addition, the carbonyl concentration in irradiated peroxide-crosslinked samples was higher, compared to the peroxide-free sample (after irradiation). Peroxide crosslinking produces tertiary carbons, therefore, the concentration of tertiary carbons increases with increasing peroxide concentration. Applicants believe that tertiary carbons are more susceptible to oxidation during irradiation. Therefore, carbonyl concentration in the irradiated peroxide-crosslinked samples increased with increasing peroxide concentration.

Figure 1B:
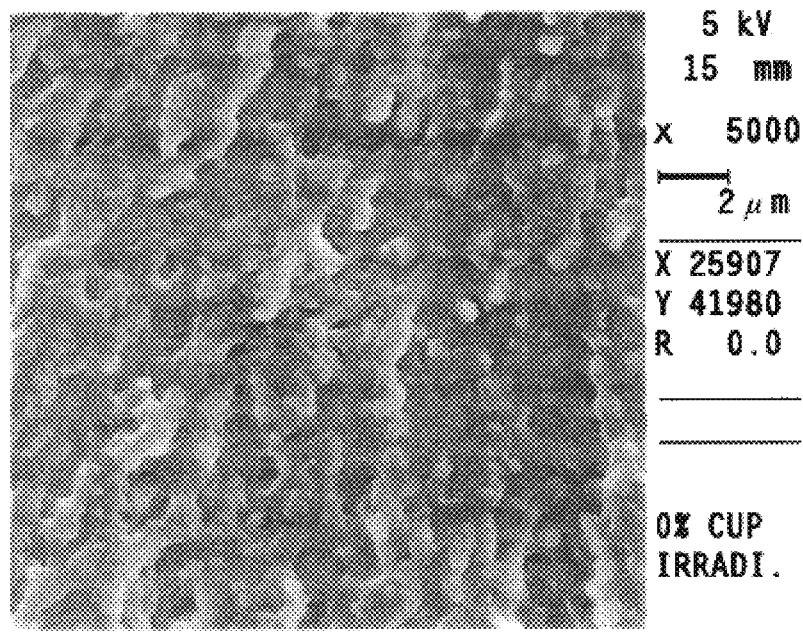
Figure 2A:
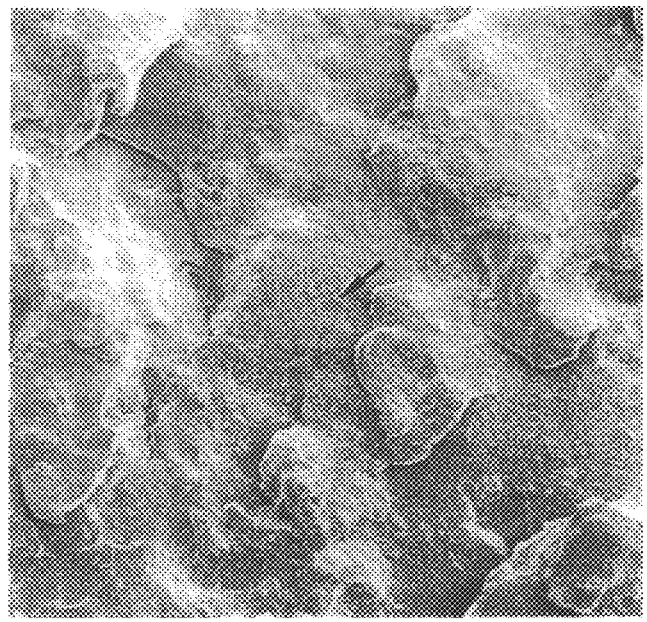
FIG. 2 presents SEM micrographs of fracture surfaces of compression molded UHMW polyethylene crosslinked with 1 wt % peroxide (after irradiation) at magnifications of (A)×200 and (B)×5000.
Figure 2B:
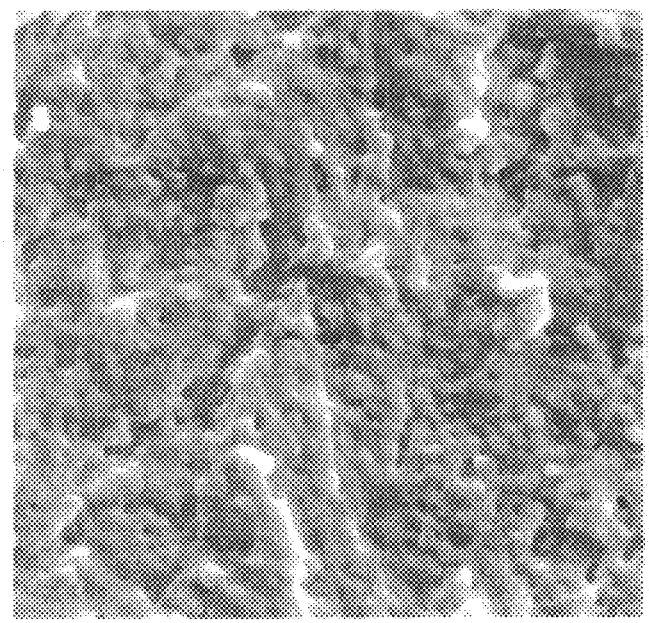

After irradiation, scanning electron micrographs were taken of the fracture surfaces of the peroxide-free and 1 wt % peroxide specimens, compression molded at 170° C. for 2 hours and subsequently slowly cooled to room temperature. The micrographs are shown in FIGS. 1 and 2, respectively. As shown in FIG. 1, a brittle (rough) fracture boundary of size comparable to that of the original UHMW polyethylene powder particles is observed. Close examination (×5000 magnification) shows an oriented nodular structure, composed of many smooth, submicron spheres. These smooth, minute spheres are believed to correspond to those present in the raw UHMW polyethylene powder and to form an aggregate. In FIG. 2, peroxide crosslinked samples show a ductile (smooth) fracture surface, compared to the rough fracture surface of peroxide-free specimen. The difference in appearance of fracture surfaces for peroxide-free and 1 wt % peroxide specimens is due to the crystallinity difference. After irradiation, the degree of crystallinity for the peroxide-free and 1 wt % peroxide specimens were 55.8 and 42%, respectively. It is believed that the peroxide-free specimen (55.8% crystallinity) suffered higher forces and less deformation during the fracturing process, leading to a sharp break in the polymer.

The crosslinking experiment was also conducted with different concentrations of Lupersol 130, using a smaller amount, 5 g, of GUR 415 and a smaller mold which was in the form of a disk. It was observed that the degree of crystallinity of the crosslinked polymer decreased with increased concentrations of Lupersol 130. The result is shown in Table 1 below:

TABLE 1

| wt % Peroxide | Crystallinity (%) Before Irradiation | Crystallinity (%) After Irradiation |
| --- | --- | --- |
| 0 | 49.2 | 55.8 |
| 0.2 | 44.0 | 50.0 |
| 0.4 | 41.6 | 46.8 |
| 0.6 | 41.3 | 46.2 |
| 0.8 | 40.0 | 45.0 |
| 1.0 | 39.8 | 42.0 |
| 1.5 | 36.8 | 36.8 |
| 2.0 | 36.5 | 36.7 |

Conclusions

Peroxide crosslinking leads to a decrease in the degree of crystallinity, peak melting temperatures, and recrystallization temperatures for 1 wt % peroxide specimen. Irradiation produces crosslinking in amorphous regions plus extensive scission of taut tie molecules and leads to increased crystallinity and crystal perfection, reduces gel content, and increases the degree of swelling of a crosslinked network.

Peroxide crosslinking reduces the effect of irradiation on the crosslinked network. This is because crosslinks introduced by peroxide crosslinking can stabilize the chain fragments resulting from the scission of taut tie molecules and suppress recrystallization of broken chains.

FTIR measurements showed that, after irradiation, the carbonyl concentration significantly increased. This is because the free radicals produced by irradiation react with oxygen dissolved and/or diffused in the polymer. In addition, carbonyl concentration in the irradiated peroxide-crosslinked samples is higher, compared to the peroxide-free sample (after irradiation). This is because peroxide crosslinking introduces tertiary carbons which are more susceptible to oxidation during irradiation, so that the carbonyl concentration in the irradiated peroxide-crosslinked samples increases.

Wide-angle x-ray scattering shows that crystal perfection increases after irradiation. It is suggested that crystal perfection is improved by irradiation-induced scission of taut tie molecules in the amorphous regions.

The peroxide-free specimen shows brittle fracture because of higher crystallinity (55.8%), whereas, the 1 wt % peroxide specimen shows ductile fracture due to lower crystallinity (42%).

Example 2

Materials and Methods

Figure 3A:
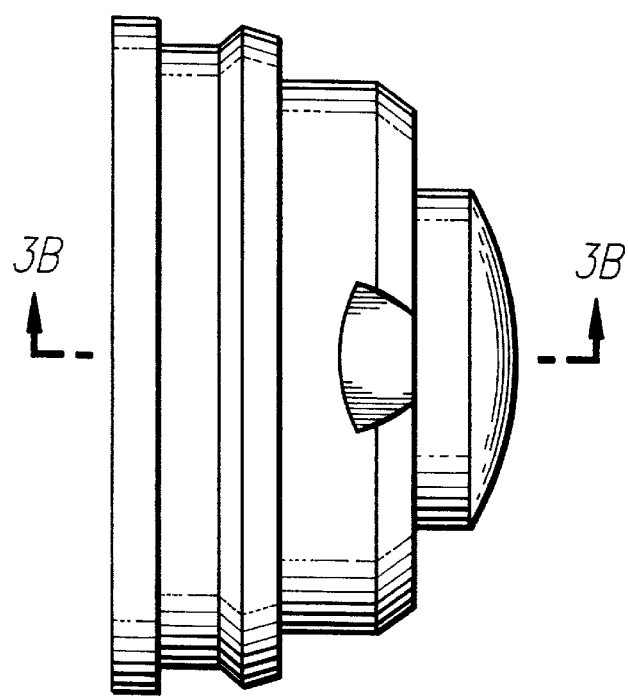
FIG. 3 presents the geometry of the acetabular cup tested for wear on the hip joint simulator used in EXAMPLE 2 below.
Figure 3B:
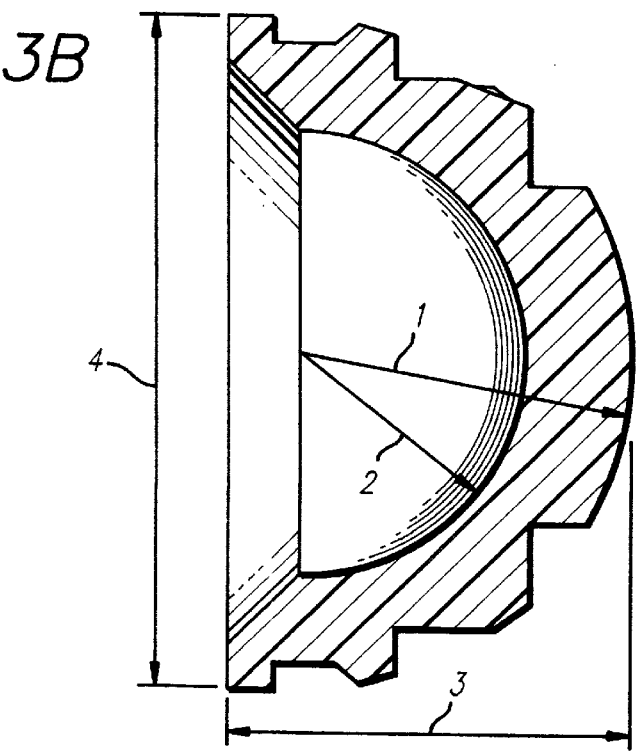
Figure 4:
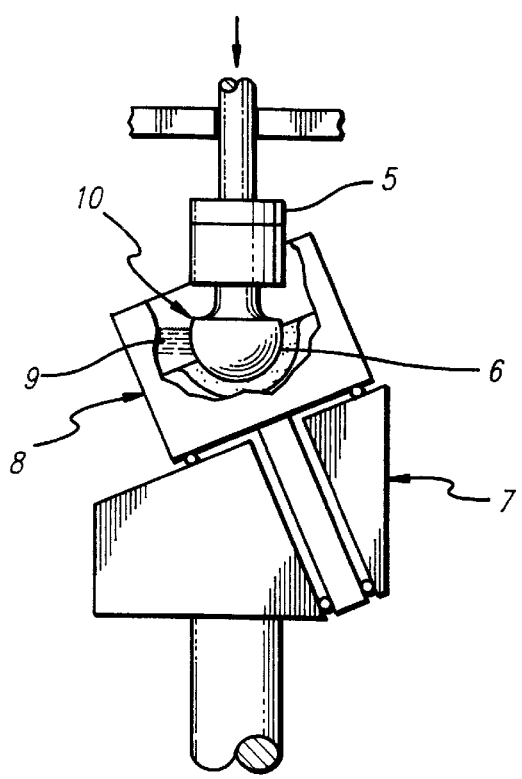
FIG. 4 presents a schematic diagram of the hip joint simulator used in EXAMPLE 2 below.

In this example, the wear resistance of the polyethylenes treated (modified) and untreated (unmodified) with peroxide in EXAMPLE 1 were tested. The control (unmodified) and modified polyethylenes were compression molded directly into the form of acetabular cups. These were then exposed to an average of approximately 3.4 Mrad of gamma radiation (SteriGenics International, Tustin, Calif.), to simulate the condition of cups that would be used in patients. Due to different amounts of post-molding shrinkage, the internal surface of each cup was machine provide nearly identical internal diameters and ball-to-cup clearances among the control and modified cups (FIG. 3). As shown in FIG. 3B, the cup's outer radius 1 is 24.5 mm, its inner radius 2 is 16.1 mm, its height 3 is 29.8 mm, and its diameter 4 is 49.0 mm The cups were pre-soaked in distilled water for three weeks prior to the wear test to minimize fluid absorption during the wear test. The wear cups were mounted on the hip joint simulator, including four cups of control polyethylene and three cups of modified polyethylene. Each cup was held in a urethane mold and mounted in a stainless steel test chamber, with a plexiglass wall to contain the bovine serum lubricant. The lubricant had 0.2% sodium azide added to retard bacterial degradation, and 20 mM ethylenediaminetetraacetic acid (EDTA) to prevent precipitation of calcium phosphate on the surfaces of the ball (McKellop, H. & Lu, B., "Friction and Wear of Polyethylene-Metal and Polyethylene-Ceramic Hip Prostheses on a Joint Simulator, Fourth World Biomaterials Congress, Berlin, Apr. 1992, 118). A polyethylene skirt covered each chamber to minimize air-borne contamination. The cups were oscillated against highly polished femoral balls of cast cobalt-chromium alloy, as used on artificial hips. The simulator applied a Paul-type cyclic load at one cycle per second {Paul, J. P., *Proc. Instn. Mech. Engrs.*, 181, Part 3J, 8–15, (1967)} with a 2000N peak, simulating the load on the human hip during normal walking, and the cups were oscillated through a bi-axial 46 degree arc at 68 cycles per minute. At intervals of 250,000 cycles, the cups were removed from the wear machine, rinsed, inspected and replaced with fresh lubricant. At 500,000 cycles and one million cycles, all of the cups were removed from the wear simulator, cleaned, dried and weighed to determine the weight loss due to wear. One million cycles is the equivalent of about one year's use of a prosthetic hip in a patient. FIG. 4 presents a schematic diagram of the hip joint simulator. The arrow indicates the direction of the computer controlled simulated physiological load exerted on the simulated hip joint. The simulator contains: a torque transducer 5, the acetabular cup 6, a dual axis offset drive block 7, a test chamber 8, serum 9, and a femoral head 10.

Three soak-correction acetabular cups of each material (control and modified) were prepared in an identical manner, but were not wear tested. These cups were mounted in a separate test frame and a cyclic load, identical to that used in the wear test, was applied. These soak-correction cups were cleaned and weighed together with the wear test cups, and the average weight gain of the correction cups was added to the apparent weight loss of the wear test cups (i.e. to correct for fluid absorption by the wear test cups that would obscure the weight loss due to wear).

Results and Discussion

Because of the apparent "negative" wear at 0.5 million cycles (discussed below), the wear rates were calculated and compared for all of the cups only for the interval from 0.5 to 1.0 million cycles. The four control polyethylene cups showed comparable amounts of wear (FIG. 5), with an average corrected wear rate of 19.19 (S. D.=2.38) milligrams per million cycles (Table 2). This was within the range that applicants have measured for cups of conventional UHMW polyethylene in a variety of studies that applicants have run.

Figure 5:
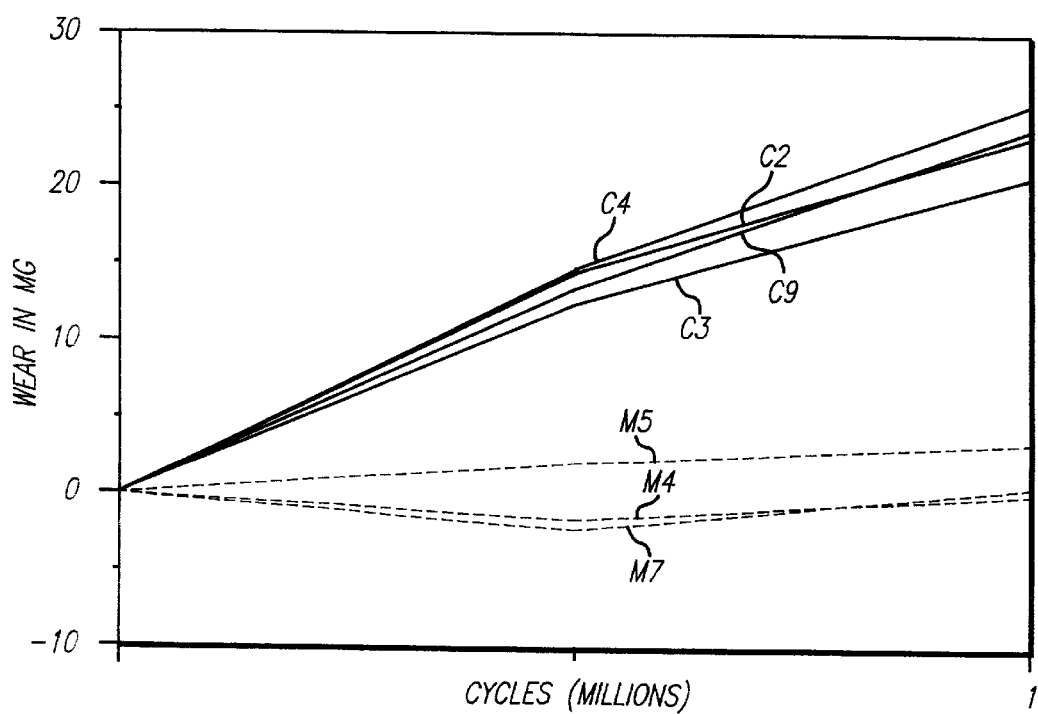
FIG. 5 presents a graph comparing the amounts of wear of the modified and unmodified UHMW polyethylene cups during a run lasting a million cycles.

The wear was much lower for the modified cups (FIG. 5). As shown in Table 2, the mean wear rate for the modified cups was 4.12 (S.D.=1.26) milligrams per million cycles, i.e. about one-fifth of the wear of the control cups. This difference was statistically significant at the level of p=0.0002).

TABLE 2

WEAR RATES
FOR CONTROL AND MODIFIED POLYETHYLENES
(INTERVAL FROM 0.5 TO 1.0 MILLION CYCLES)

| MATERIAL | CUP NUMBER | WEAR RATE (mg/million cycles) | MEAN WEAR RATE (STANDARD DEVIATION) |
|---|---|---|---|
| CONTROL POLYETHYLENE | C2 | 21.67 | 19.19 |
| | C3 | 16.78 | (2.38) |
| | C4 | 17.57 | |
| | C9 | 20.76 | |
| MODIFIED POLYETHYLENE | M4 | 4.08 | 4.12 |
| | M5 | 2.88 | (1.26) |
| | M7 | 5.39 | |

For the data point at 0.5 million cycles, the corrected weights were lower than the weights before the wear test. This was most likely the result of the wear being very small, and the fluid absorption by the test cups being slightly greater than the average gain of the soak correction cups, such that the correction factor did not entirely offset the fluid gain by the wear cups (giving an apparent "negative" wear). A small difference in water absorption rates between the wear cups and the correction cups could arise due to differences in equilibrium temperatures (the wear cups were typically at 35° C. to 45° C., whereas the soak correction cups were at room temperature, about 20° C.), due to mechanical agitation of the serum during oscillation of the wear test chambers, or other causes.

Example 3

During the wear test in the simulator described in EXAMPLE 2, it was discovered that the acetabular cups shrunk at simulated human body temperature. In order to stabilize the shrinkage, in this experiment (unrelated to EXAMPLE 2), the cups were annealed at 100° C. in a vacuum oven for 2 hours. After annealing, the total shrinkage in diameter for uncrosslinked and crosslinked cups was approximately 1% and 2%, respectively. The degrees of crystallinity of the annealed cups were determined by DSC. The degree of crystallinity of the uncrosslinked polymer was unchanged, whereas that of the crosslinked polymer was increased by approximately 1%. To test for further shrinkage, the cups were again put in the vacuum oven at 80° C. for two hours, and no further shrinkage was observed.

The present invention has been described with reference to specific embodiments. However, this application is intended to cover those changes and substitutions which may be made by those skilled in the art without departing from the spirit and scope of the appended claims.

We claim:

1. In a medical implant having at least a first member and a bearing component providing a bearing contact surface for the first member, the bearing component made of crosslinked ultrahigh molecular weight polyethylene and wherein said crosslinked ultrahigh molecular weight polyethylene is characterized by a polymeric structure of about 51% crystallinity or less.

2. The medical implant of claim 1, wherein crosslinking is achieved according to the method selected from the group consisting of: chemically crosslinking a polyethylene, irradiation crosslinking a polyethylene, and photocrosslinking a polyethylene.

3. The medical implant of claim 1, wherein said implant is further irradiated in the solid state for sterilization.

4. The medical implant of claim 3, wherein said implant is irradiated in air at a sterilization dose.

5. The medical implant of claim 2, wherein said crosslinked ultrahigh molecular weight polyethylene is further characterized by its lack of shrinkage.

6. The medical implant of claim 1, wherein said crosslinked ultrahigh molecular weight polyethylene is characterized by a polymeric structure of about 3.4 degree of swelling or less.

7. A medical implant bearing component with improved wear resistance for use within a joint prosthesis within a body, said implant bearing component is made of a crosslinked ultrahigh molecular weight polyethylene having a polymeric structure of about 51% crystallinity or less, so as to increase wear resistance of said implant within the body.

8. The medical implant bearing component of claim 7, wherein said crosslinked ultrahigh molecular weight polyethylene is further characterized by a polymeric structure of about at least 97% gel content.

9. The medical implant bearing component of claim 7, wherein said ultrahigh molecular weight polyethylene is further characterized by a smooth fracture surface, decreased tensile strength at break point, and decreased Young's modulus compared to a corresponding uncrosslinked ultrahigh molecular weight polyethylene.

10. The medical implant bearing component of claim 7, wherein crosslinking is achieved according to the method selected from the group consisting of: chemically crosslinking a polyethylene, irradiation crosslinking a polyethylene, and photocrosslinking a polyethylene.

11. The medical implant bearing component of claim 10, wherein the medical implant is further irradiated in air at a sterilization dose in its solid state.

12. The medical implant bearing component of claim 11, wherein said ultrahigh molecular weight polyethylene has about 45% crystallinity or less.

13. The medical implant bearing component of claim 12, wherein the crosslinked ultrahigh molecular weight polyethylene is further characterized by a lack of shrinkage.

14. The medical implant bearing component of claim 13, wherein said implant is an orthopaedic bearing component for use in hip or knee joint replacement.

15. A medical implant bearing component with improved wear resistance for use within a joint prosthesis within a body, said component is made of a crosslinked ultrahigh molecular weight polyethylene having a polymeric structure of about 3.4 degree of swelling or less so as to increase the wear resistance of said implant within the body.

16. An orthopaedic material for production of medical implant bearing component with improved wear resistance for use within a joint prosthesis within a body, comprising crosslinked ultrahigh molecular weight polyethylene having a polymeric structure characterized by: about 51% crystallinity or less.

17. The orthopaedic material of claim 16, wherein crosslinking is achieved according to the method selected from the group consisting of: chemically crosslinking a polyethylene, irradiation crosslinking a polyethylene, and photocrosslinking a polyethylene.

18. An orthopaedic material for production of medical implant bearing component with improved wear resistance for use within a joint prosthesis within a body, comprising crosslinked ultrahigh molecular weight polyethylene having a polymeric structure characterized by about 3.4 degree of swelling or less.

19. A fabricated article with improved wear resistance being made into a medical implant bearing component made of crosslinked ultrahigh molecular weight polyethylene having a polymeric structure characterized by about 51% crystallinity or less, wherein said article is further annealed to preshrink its size and to alter its physical structure such that its size is stabilized before being made into said medical implant bearing component.

20. The fabricated article of claim 19, wherein said medical implant bearing component is characterized by its resistance to in vivo wear despite having been irradiated in air at a sterilization dose in a solid state.

21. A method for improving the wear characteristics of an implantable orthopaedic bearing component made from ultrahigh molecular weight polyethylene comprising the step of crosslinking a polyethylene to provide a polymeric structure with about 51% or less crystallinity.

22. A method for improving the wear characteristics of an implantable orthopaedic bearing component made from ultrahigh molecular weight polyethylene comprising the step of crosslinking a polyethylene to provide a polymeric structure with about 3.4 degree of swelling or less.

23. A method for making an implantable orthopaedic bearing component for use in a joint prosthesis in a body so as to reduce its wear, comprising the steps of: (a) crosslinking a polyethylene to provide a crosslinked ultrahigh molecular weight polyethylene with a polymeric structure of about 51% or less crystallinity, and (b) forming the implantable orthopaedic bearing component from said crosslinked ultrahigh molecular weight polyethylene.

24. A method for making an implantable orthopaedic bearing component for use in a joint prosthesis in a body so as to reduce its wear, comprising the steps of: (a) crosslinking a polyethylene to provide a crosslinked ultrahigh molecular weight polyethylene with a polymeric structure of about 3.4 degree of swelling or less, and (b) forming the implantable orthopaedic bearing component from said crosslinked ultrahigh molecular weight polyethylene.

25. The medical implant bearing component of claim 7, wherein said crosslinked ultrahigh molecular weight polyethylene is characterized by a polymeric structure of about 3.4 degree of swelling or less.

26. The orthopaedic material of claim 16, wherein the polymeric structure is characterized by a about 3.4 degree of swelling or less.

27. The fabricated article of claim 19, wherein the polymeric structure is characterized by a about 3.4 degree of swelling or less.

28. The method of claim 21, wherein the crosslinking occurs with about 3.4 degree of swelling or less.

29. The medical implant of claim 1, wherein said crosslinked ultrahigh molecular weight polyethylene is further characterized by a polymeric structure of about at least 97% gel content.

30. The medical implant of claim 6, wherein said crosslinked ultrahigh molecular weight polyethylene is further characterized by a polymeric structure of about at least 97% gel content.

31. The medical implant bearing component of claim 25, wherein said crosslinked ultrahigh molecular weight polyethylene is further characterized by a polymeric structure of about at least 97% gel.

32. The medical implant of claim 1, wherein the implant is a hip prosthesis, said first member is a femoral component and said bearing component is an acetabular component.

33. The medical implant bearing component of claim 15, wherein the joint prosthesis is a hip prosthesis and said implant is an acetabular component which cooperates with a femoral component.

34. The orthopaedic material of claim 16, wherein the joint prosthesis is a hip prosthesis and said implant is an acetabular component which cooperates with a femoral component.

35. The orthopaedic material of claim 18, wherein the joint prosthesis is a hip prosthesis, the bearing component is an acetabular component which cooperates with a femoral component.

36. The method of claim 21, wherein the bearing component is attached to an acetabular component of a hip prosthesis for abutting contact with a femoral component.

37. The method of claim 22, wherein the bearing component is attached to an acetabular component of a hip prosthesis for abutting contact with a femoral component.

38. The method of claim 23, wherein the bearing component is attached to an acetabular component of a hip prosthesis for abutting contact with a femoral component.

39. In a medical implant having at least a first member and a bearing component providing a bearing contact surface for the first member, the bearing component made of crosslinked ultrahigh molecular weight polyethylene and wherein said crosslinked ultrahigh molecular weight polyethylene is characterized by a polymeric structure of about 3.4 degree of swelling or less.

40. The medical implant of claim 39, wherein said crosslinked ultrahigh molecular weight polyethylene is further characterized by a polymeric structure of about at least 97% gel.

41. The medical implant of claim 39, wherein the implant is a hip prosthesis, said first member is a femoral component and said bearing component is an acetabular component.

42. The medical implant of claim 39, wherein crosslinking is achieved according to the method selected from the group consisting of: chemically crosslinking a polyethylene, irradiation crosslinking a polyethylene, and photocrosslinking a polyethylene.

43. The medical implant of claim 42, wherein said implant is further irradiated in the solid state for sterilization.

44. The medical implant of claim 43, wherein said implant is irradiated in air at a sterilization dose.

45. The medical implant of claim 42, wherein said crosslinked ultrahigh molecular weight polyethylene is further characterized by its lack of shrinkage.

46. A fabricated article with improved wear resistance being made into a medical implant bearing component made of crosslinked ultrahigh molecular weight polyethylene having a polymeric structure characterized by about 3.4 degree of swelling or less, wherein said article is further annealed to preshrink its size and to alter its physical structure such that its size is stabilized before being made into said medical implant bearing component.

47. The fabricated article of claim 46, wherein said medical implant bearing component is characterized by its resistance to in vivo wear despite having been irradiated in air at a sterilization dose in a solid state.

48. The method of claim 24, wherein the bearing component is attached to an acetabular component of a hip prosthesis for abutting contact with a femoral component.

49. The medical implant of claim 15, wherein said crosslinked ultrahigh molecular weight polyethylene is further characterized by a polymeric structure of about 45% crystallinity or less.

50. The medical implant of claim 15, wherein said crosslinked ultrahigh molecular weight polyethylene is further characterized by a polymeric structure of about at least 97% gel.

51. The medical implant of claim 15, wherein said ultrahigh molecular weight polyethylene is further characterized by a smooth fracture surface, decreased tensile strength at break point, and decreased Young's modulus compared to a corresponding uncrosslinked ultrahigh molecular weight polyethylene.

52. The medical implant of claim 15, wherein the crosslinked ultrahigh molecular weight polyethylene is crosslinked according to the method selected from the group consisting of: chemically crosslinking a polyethylene, irradiation crosslinking a polyethylene, and photocrosslinking a polyethylene.

53. The medical implant of claim 52, wherein the medical implant is further irradiated in air at a sterilization dose in its solid state.

54. The medical implant of claim 53, wherein said ultrahigh molecular weight polyethylene has about 45% crystallinity or less.

55. The medical implant of claim 54, wherein the crosslinked ultrahigh molecular weight polyethylene is further characterized by a lack of shrinkage.

56. The medical implant of claim 55, wherein said implant is an orthopaedic bearing component for use in hip or knee joint replacement.

57. The medical implant bearing component of claim 49, wherein the joint prosthesis is a hip prosthesis and said implant is an acetabular component which cooperates with a femoral component.

58. The orthopaedic material of claim 18, wherein the crosslinked ultrahigh molecular weight polyethylene is crosslinked according to the method selected from the group consisting of: chemically crosslinking a polyethylene, irradiation crosslinking a polyethylene, and photocrosslinking a polyethylene.

59. The method of claim 21, further comprising the steps of producing a fabricated article made of the crosslinked ultrahigh molecular weight polyethylene, annealing the fabricated article to preshrink its size and to alter its physical structure such that its size is stabilized before being made into said implantable orthopaedic bearing component.

60. The method of claim 22, further comprising the steps of producing a fabricated article made of the crosslinked ultrahigh molecular weight polyethylene, annealing the fabricated article to preshrink its size and to alter its physical structure such that its size is stabilized before being made into said implantable orthopaedic bearing component.

61. The medical implant of claim 1, wherein the medical implant is a prosthesis selected from the group consisting of: hip, knee, ankle, elbow, jaw, shoulder, finger and spine prostheses.

62. The medical implant bearing component of claim 7, wherein the joint prosthesis is selected from the group consisting of: hip, knee, ankle, elbow, jaw, shoulder, finger and spine prostheses.

63. The medical implant bearing component of claim 15, wherein the joint prosthesis is selected from the group consisting of: hip, knee, ankle, elbow, jaw, shoulder, finger and spine prostheses.

64. The orthopaedic material of claim 16, wherein the joint prosthesis selected from the group consisting of: hip, knee, ankle, elbow, jaw, shoulder, finger and spine prostheses.

65. The orthopaedic material of claim 18, wherein the joint prosthesis is selected from the group consisting of: hip, knee, ankle, elbow, jaw, shoulder, finger and spine prostheses.

66. The fabricated article of claim 19, wherein the bearing component is for use in a joint prosthesis selected from the group consisting of: hip, knee, ankle, elbow, jaw, shoulder, finger and spine prostheses.

67. The fabricated article of claim 39, wherein the bearing component is for use in a joint prosthesis selected from the group consisting of: hip, knee, ankle, elbow, jaw, shoulder, finger and spine prostheses.

68. The fabricated article of claim 46, wherein the bearing component is for use in a joint prosthesis selected from the group consisting of: hip, knee, ankle, elbow, jaw, shoulder, finger and spine prostheses.

69. The method of claim 21, wherein the implantable orthopaedic bearing component is for use in a joint prosthesis selected from the group consisting of: hip, knee, ankle, elbow, jaw, shoulder, finger and spine prostheses.

70. The method of claim 22, wherein the implantable orthopaedic bearing component is for use in a joint prosthesis selected from the group consisting of: hip, knee, ankle, elbow, jaw, shoulder, finger and spine prostheses.

71. The method of claim 23, wherein the implantable orthopaedic bearing component is for use in a joint prosthesis selected from the group consisting of: hip, knee, ankle, elbow, jaw, shoulder, finger and spine prostheses.

72. The method of claim 24, wherein the implantable orthopaedic bearing component is for use in a joint prosthesis selected from the group consisting of: hip, knee, ankle, elbow, jaw, shoulder, finger and spine prostheses.

* * * * *